US008116882B2

(12) United States Patent
Kowalczewski

(10) Patent No.: US 8,116,882 B2
(45) Date of Patent: Feb. 14, 2012

(54) ADJUSTABLE TISSUE OR NERVE CUFF AND METHOD OF USE

(75) Inventor: Jan Kowalczewski, Edmontdon (CA)

(73) Assignee: Angeltear Solutions Inc., Edmonton (CA)

( * ) Notice: Subject to any disclaimer, the term of this patent is extended or adjusted under 35 U.S.C. 154(b) by 343 days.

(21) Appl. No.: 12/370,364

(22) Filed: Feb. 12, 2009

(65) Prior Publication Data

US 2009/0210042 A1      Aug. 20, 2009

Related U.S. Application Data

(60) Provisional application No. 61/029,269, filed on Feb. 15, 2008.

(51) Int. Cl.
*A61N 1/00* (2006.01)
(52) U.S. Cl. ........................................ 607/118
(58) Field of Classification Search .................... 607/118
See application file for complete search history.

(56) References Cited

U.S. PATENT DOCUMENTS

| | | | |
|---|---|---|---|
| 3,654,933 A | 4/1972 | Hagfors | |
| 3,738,368 A | 6/1973 | Avery | |
| 3,874,034 A * | 4/1975 | Clayton | 24/30.5 P |
| 4,535,764 A * | 8/1985 | Ebert | 606/74 |
| 4,602,624 A | 7/1986 | Naples et al. | |
| 5,038,781 A | 8/1991 | Lynch | |
| 5,487,756 A | 1/1996 | Kallesoe et al. | |
| 5,505,201 A | 4/1996 | Grill, Jr. et al. | |
| 5,634,462 A | 6/1997 | Tyler et al. | |
| 5,913,882 A | 6/1999 | King | |
| 5,964,702 A | 10/1999 | Grill, Jr. et al. | |
| 6,600,956 B2 | 7/2003 | Maschino et al. | |
| 7,072,720 B2 | 7/2006 | Puskas | |
| 7,266,885 B1 | 9/2007 | Swanson | |
| 2005/0148814 A1 * | 7/2005 | Fischi et al. | 600/37 |
| 2006/0184211 A1 | 8/2006 | Gaunt et al. | |

FOREIGN PATENT DOCUMENTS

| | | |
|---|---|---|
| WO | WO 93/20887 | 10/1993 |
| WO | WO 01/22877 | 4/2001 |
| WO | WO 2006/017634 | 2/2006 |
| WO | WO 2007/082382 | 7/2007 |
| WO | WO 2007/140597 | 12/2007 |

OTHER PUBLICATIONS

Andreasen, LNS et al. (1998) "On the importance of configuration and closure of nerve cuff electrodes for recording"; *Proceedings 20th Ann.Int.Conf. IEEE* 20(6):3004-3007.
Int. Search Report and Written Opinion PCT/CA2009/000171.

* cited by examiner

*Primary Examiner* — George Manuel
(74) *Attorney, Agent, or Firm* — Greenlee Sullivan P.C.

(57) ABSTRACT

An implantable adjustable body tissue cuff, apparatus and method. The cuff is an elastomeric strap of biocompatible non-conductive material. The strap's tail and head provide adjustable length fastening by a) the tail being formed with longitudinally spaced, laterally paired locking projections and the head being formed with one or more locking apertures; or b) the tail being formed with longitudinally spaced locking apertures and the head being formed with one or more laterally paired locking projections. The locking projection shape allows for passage through the locking aperture, while restricting movement in a reverse direction. The cuff accommodates devices such as tissue stimulators or recorders, with conductive elements attached, imbedded, or printed on the strap body. The cuff is intra-operatively adjusted to optimize placement and contact between conductive elements and body tissue, without tissue damage. This cuff accommodates varying tissue diameters and simplifies manufacture and surgical placement.

21 Claims, 10 Drawing Sheets

ADJUSTABLE TISSUE OR NERVE CUFF AND METHOD OF USE

CROSS-REFERENCE TO RELATED APPLICATION

This application claims priority from U.S. Provisional Patent Application No. 61/029,269 filed Feb. 15, 2008, which is incorporated by reference herein in its entirety to the extent that there is no inconsistency with the present disclosure.

BACKGROUND OF THE INVENTION

The invention relates to the field of surgically implantable devices and methods in the biomedical field. Implantable cuffs have been used for the stimulation and recording of biological tissues, particularly nerves. Stimulation of the nervous system with nerve cuffs can result in recovery of lost sensory or motor function in individuals with neurological deficits. An example of such an application is the Freehand™stimulator (Neurocontrol Corporation, Ohio, USA) that can restore a degree of hand function in an individual with a spinal cord injury. Recording has also been performed with implantable cuffs. Recording nerve function can relay vital information back to a processor that assists in decision-making based on the activity of the nerve. For example, in sleep apnea, patients implanted with nerve cuffs rely on the nerve cuff to be used for recording as well as stimulation when necessary. By targeting a nerve with an implanted nerve cuff, much less electrical current is required than for intra-muscular stimulation or surface stimulation. Intramuscular stimulation involves using an electrode directly in the muscle, whereas surface stimulation utilizes electrodes at the skin surface to activate nerves in the general area of interest. Surface stimulation is much less selective of the muscles it can stimulate as compared to nerve cuffs.

Most implantable electro-neuroprosthetics that target peripheral nerves use some type of nerve cuff. Currently there are three primary types of nerve cuffs used to stimulate nerves with an electro-neuroprosthesis, namely C-shaped cuffs, helical cuffs, and nerve reshaping cuffs.

C-shaped nerve cuff electrodes are named for their c-shaped cross section. They range from split cylinder, spiral and multi-compartmental designs. An example is seen in U.S. Pat. No. 6,600,956 to Maschino et al. Generally the cuff is made of an electrically insulative substrate with one or more imbedded electrically conductive elements designed to interact electrically with the nerve. The preferred substrate is biocompatible, the most common material being silicone rubber. The main draw back to c-shaped nerve cuffs is that the internal diameter of the nerve cuff needs to be estimated prior to the surgery, and hence it can result in loose fitting cuffs if made too large, or too constricting cuffs resulting in nerve damage if made too small. This can greatly increase costs as multiple sizes need to be made available to the surgeon to minimize problems. Spiral electrodes that are self curling alleviate the size problem and can be removed with minimal force.

Helical cuffs such as shown in U.S. Pat. No. 5,964,702 to Grill et al. are built much like spiral cuffs from a self curling substrate, but they are cut to look like a spring. One main draw back is that they need to be wrapped around the nerve, which can be a time consuming process. Furthermore, helical cuffs rely entirely on the substrate properties to close properly as there is no closing mechanism. This can result in inappropriate contacts being made to the nerve. Helical cuffs are also susceptible to size constraints.

Nerve reshaping cuffs reshape the nerve to fit the cuff's internal space. An example of a nerve reshaping cuff is illustrated in U.S. Pat. No. 5,634,462 to Tyler et al. This type of cuff relies on a force being applied to the nerve itself to squeeze it into a desired shape, either by using rigid structures or corrugations in the nerve cuff. If appropriate pressure is used, and enough space provided for the nerve, there is a possibility of using multiple electrically conductive units to isolate and stimulate only certain parts of the nerve. However, one risk is that damage to the nerve can occur during the installation. As well, a possible tensile strength decrease can weaken the nerve. In the case of large rigid structures near the nerve there is a further risk for increasing the incidence of inflammation in response to the mechanical aggravation of the tissues. The rigidity needed to shape the nerve in a corrugated nerve cuff such as in U.S. Pat. No. 5,634,462 also limits the ability of the cuff to accommodate different nerve sizes, so as above, different size cuffs must be provided for different nerve sizes. Adjusting the cuff intra-operatively to re-position conductive elements, or to adjust for size, is resisted by the design and rigidity of the structure. Finally, the corrugations of this type of device are designed to minimize contact points with the nerve, which for some applications limits the nerve surface which can be directly contacted with electrical contacts of nerve interacting devices.

In spite of the large number of available nerve cuff designs, there remains a need for an adjustable size tissue cuff, that can be quickly installed, intra-operatively adjusted, and which places just the right amount of pressure on the nerve or tissue to allow for ideal contact with conductive units without damaging the nerve. As well, given the many different functional electrical devices currently available that rely on peripheral nerve stimulation, there is a further need for a nerve cuff that is not limited to a single type of electrode lead design.

SUMMARY OF INVENTION

In one broad aspect, the invention provides an implantable, circumferentially adjustable tissue cuff for circumferential attachment to an internal body tissue. The cuff includes a flat, thin, elastomeric strap formed of a biocompatible non-conductive material, the strap being elongated along a longitudinal axis, the strap having a body portion connected between a tail end portion and a head end portion and a length in excess of a circumference of the body tissue. The tail end portion and the head end portion are configured for adjustable length fastening one to the other when wrapped around the body tissue. Either of the following configurations may be included:

a) The tail end portion may be formed with a plurality of longitudinally spaced, laterally paired locking projections while the head end portion is formed with one or more locking apertures; or b) The tail end portion may be formed with a plurality of longitudinally spaced locking apertures while the head end portion is formed with one or more laterally paired locking projections.

In either configuration, each of the laterally paired locking projections is shaped to allow for passage through the locking apertures by flexing of the locking projections in an insertion direction through the locking aperture, and to restrict movement in a reversing direction through the locking aperture.

In another broad aspect, the invention provides a tissue cuff apparatus to enable circumferential attachment of a tissue interacting device to an internal body tissue. The apparatus includes the above tissue cuff and one or more implantable tissue interacting devices attached to, imbedded in, or printed on the body portion of the strap. The tissue interacting device includes one or more conductive elements adapted to be in conducting proximity to the body tissue when the strap is wrapped around the body tissue. The tissue interacting device may be one adapted to stimulate or record the body tissue, in which case, the conductive element is adapted to respond to one or more of electrical, thermal, auditory, vibrational, light or fluid stimulation. A type of conductive element is one or more electrical contacts on an inner face of the body portion of the strap. The apparatus may include insulated leads connecting the electrical contacts to a remote stimulating or recording device. An exemplary tissue interacting device is an implanted conductor or electrode lead adapted to be held in contact with the body tissue by the strap. Another exemplary tissue interacting device is a wireless stimulator attached to the strap, or held within the strap.

In yet another broad aspect, the invention provides a method for circumferential attachment of a tissue cuff to an internal body tissue, the method comprising the steps of:

i. providing a tissue cuff as described above;
ii. wrapping the strap around the body tissue; and
iii. fastening the tail end portion and the head end portion together with an appropriate one of the laterally paired locking projection and locking apertures, whereby the plurality of locking apertures or the plurality of laterally paired projections allows for a circumference of the tissue cuff to be adjusted intra-operatively for a particular circumference of the body tissue.

The method thus provides an intra-operative technique to adjust cuff size around biological tissues, with the option to secure and lock the cuff to a desired size. Multiple sized nerve cuffs are no longer needed since during the implantation the cuff can be tightened or loosened for the best fit. This tissue cuff allows for intra-operative fine tuning. Test stimulations can be carried out and if an inappropriate result is seen the cuff can be moved or readjusted with ease to yield a better result, without tissue damage. Furthermore the cuff can be locked, stitched shut and/or anchored to nearby tissues to minimize migration of the cuff and potential failure.

Unlike other nerve cuff designs, the cuff of this invention enables simple manufacture with a simple planar 2D process from a flat sheet of substrate material. It can be stamped or laser cut from a flat biocompatible sheet of non-conductive material. The body portion of the cuff may then be attached to conductive elements such as electrode leads. The planar nature of the cuff apparatus also allows for photolithography and electroplating to be used in generating custom conductive elements and electronic circuits onto the body portion of the cuff. The cuff simplicity and size are conducive to endoscopic placement of this invention.

DETAILED DESCRIPTION OF THE INVENTION

Figure 1:
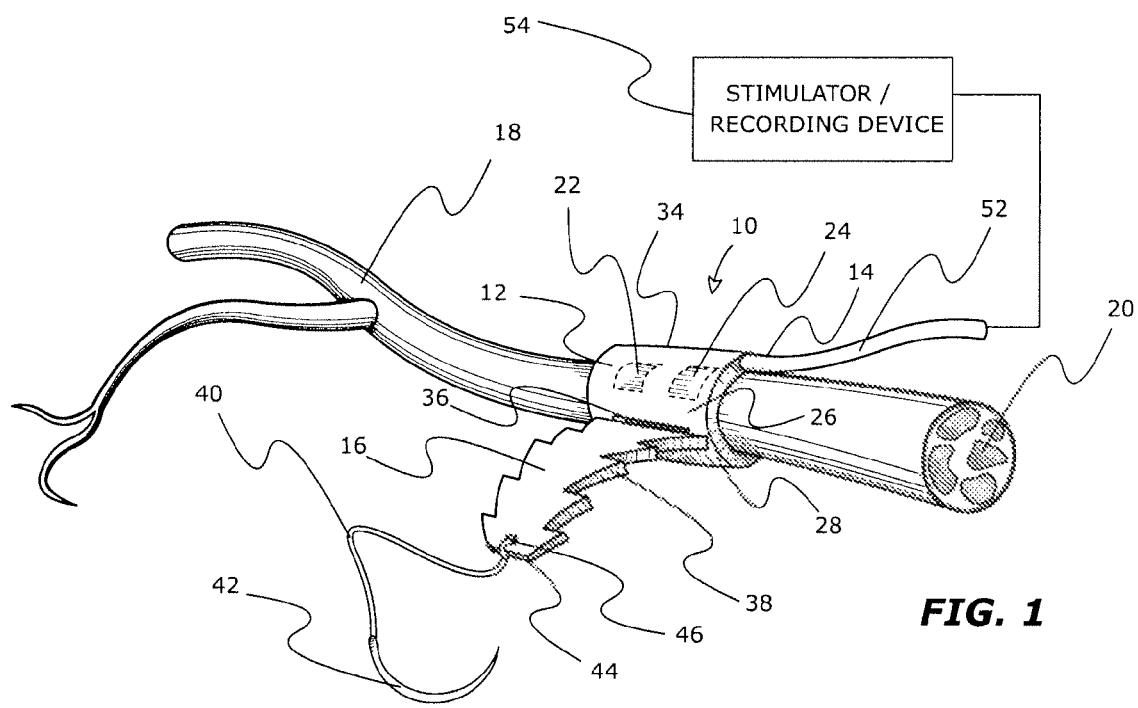
FIG. 1 is a schematic perspective view of one embodiment of the invention, showing the nerve cuff wrapped around a nerve and fastened with the adjustable closing mechanism. The figure shows a nerve interacting device in the form of conductive elements on the inner face of the nerve cuff and insulated leads to a stimulator or recording device.

The embodiments of the present invention are described by way of example only and with reference to the figures in which similar reference numerals are used in different figures to denote similar components. The tissue cuff of the figures is shown in the form of a nerve cuff, but the invention has broad application to other internal body tissues such as veins and arteries or other body tissues which can be encircled with a tissue cuff apparatus for purposes such as healing, attaching other devices or tissues, or immobilizing. While some dimensions are provided herein, the dimensions are non-limiting, and are provided as exemplary guidelines for preferred embodiments involving nerves, where typical nerve circumferences may be about 3 to 5 mm in diameter.

Figure 19:
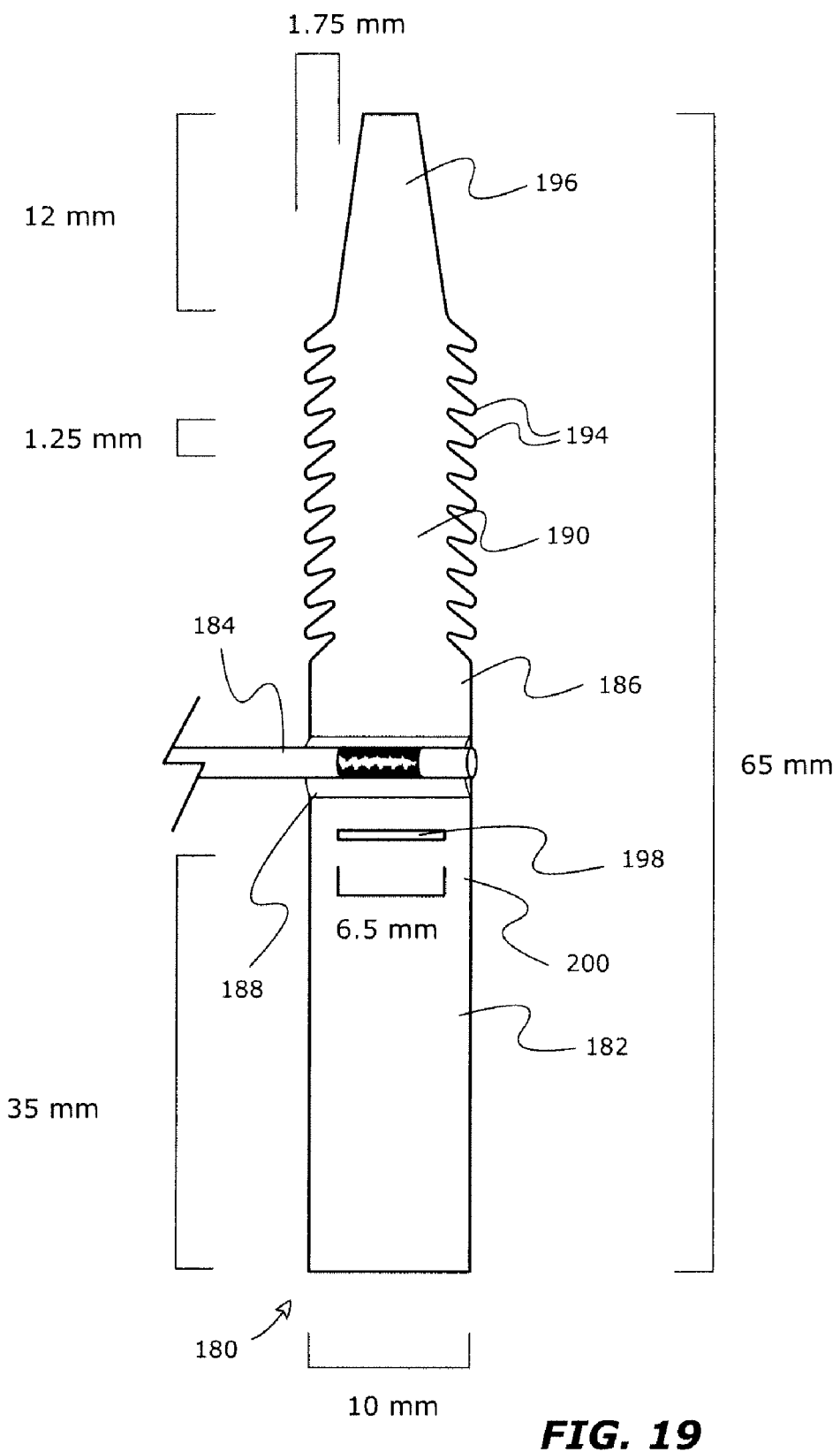
FIG. 19 is a schematic plan view of the inner face of the nerve cuff apparatus used in the example of this application with an implanted conductor for nerve stimulation. Exemplary but non-limiting dimensions are provided on the figure.

The nerve cuff apparatus of this invention as illustrated in FIGS. 1-6 is shown generally at 10, and includes a nerve cuff 12 and a nerve interacting device 14. The nerve cuff 12 consists of a strap 16 formed of a thin, flat sheet of a non-conductive, biocompatible, elastomeric material that can be wrapped around a peripheral nerve 18. The nerve 18 is usually composed of multiple fascicles 20, so adjustment of the nerve interacting device 14, relative to the fascicles 20 may be desired during implantation (i.e., intra-operatively). The nerve interacting device 14 includes conductive elements (in this case electrode units) 22, 24 imbedded in the strap 16 (or printed or attached) direct contact to the nerve 18. The non-conductive properties of the elastomeric material ensures that surrounding body tissue is insulated from the electrode units 22, 24. The strap 16 is elongated with a longitudinal axis along its length dimension, and a transverse width dimension. The length dimension is longer than that needed to wrap around the body tissue of interest. The width dimension is sufficient to provide structural support for the nerve interacting device of interest and sufficient to be manipulated during implantation. The width dimension (which may be constant over the length, or varied) of the strap 16 will depend on the thickness of the strap 16, and the particular application for the nerve cuff apparatus 10. The strap 16 is thin. For nerve applications, the strap thickness is preferably less than about 1 mm, more preferably less than about 0.5 mm, and still more preferably between about 0.15-0.35 mm. The strap 16 is sufficiently thin that it remains elastic, pliable and flexible for implanting, fastening, and adjusting. One set of exemplary, non-limiting dimensions for nerves of about 3 to 5 mm diameter is shown in FIG. 19.

Figure 2:
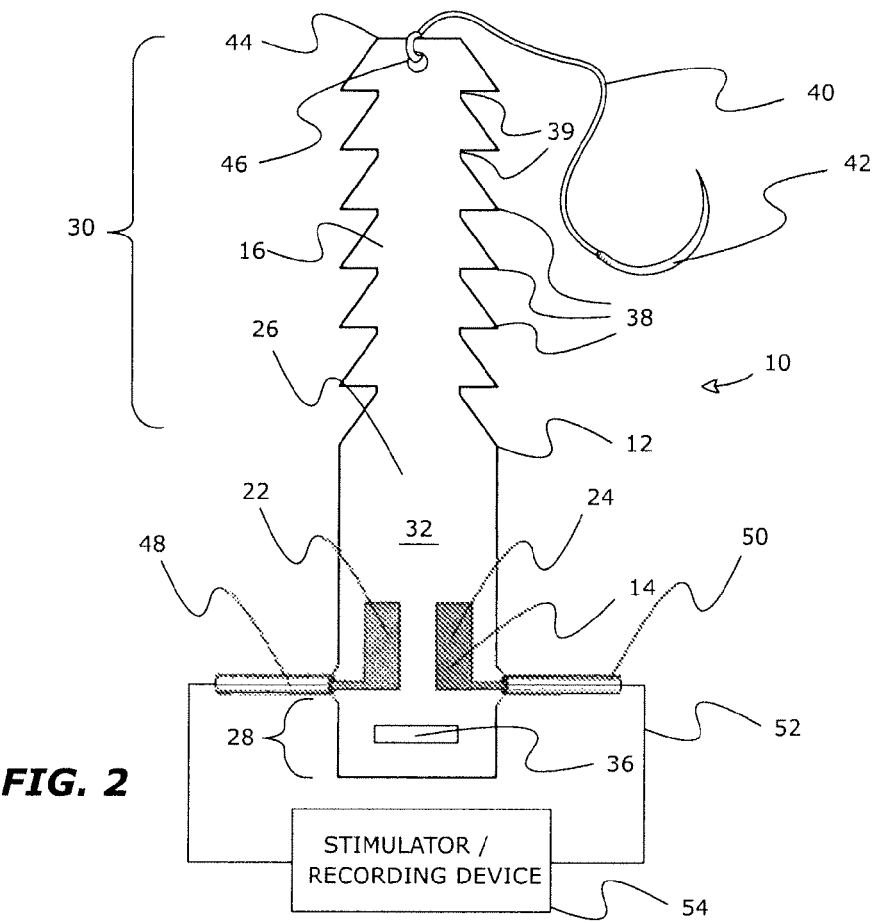
FIG. 2 is a schematic plan view of the inner face of the nerve cuff of FIG. 1, showing the cuff and conductive elements connected to the stimulator or recording device.

The strap 16 includes a body portion 26 connected between (preferably integral with) a head end portion 28 and a tail end portion 30 (best seen in FIG. 2). The body portion 26 has an inner face 32 which faces the nerve to be encircled, and an outer face 34 which faces surrounding body tissues after implantation. The head and tail end portions 28, 30 are configured for adjustable length fastening one to the other around the nerve 18, and thus provide the adjustable locking or closing mechanism of this invention. This leaves the body portion 26 isolated and remote from the adjustable length ends 28, 30, for stable and secure attachment to the nerve 18, and for separate and secure attachment to one or more nerve interacting devices 14. The adjustable length fastening is generally achieved by providing the extra length (i.e., a total length of the strap 16 which is in excess of an expected circumference of a body tissue to be encircled) in one or both of the head and tail end portions 28, 30. In general, the length of the body portion 26 will not be greater than the expected circumference of the body tissue to be encircled, so the extra length is provided in one or both of the head and tail end portions 28, 30 to ensure a secure attachment to the body tissue. In applications where the body tissue is very small, such as nerves, providing extra length in both the head and tail end portions 28, 30 may be advantageous to assist in placement and manipulation during implantation.

The head end portion 28 is shown in the embodiment of FIGS. 1-6 to be formed with a transverse slot 36 as a locking aperture. The tail end portion 30 is formed with a plurality of longitudinally spaced laterally paired locking projections 38. The paired locking projections 38 are spaced by narrower neck portions 39. The locking projections 38 are shaped to allow for passage through the slot 36 by flexing in an insertion direction (i.e., in the direction of threading through the slot 36 to fasten around the nerve 18), and to restrict movement in the reversing direction through the slot 36 (i.e., in the direction to loosen the strap 16). The flexibility of the projections 38 permits them to be re-adjusted by the surgeon during implantation in the reverse direction if needed, but once the appropriate position is achieved, the projections 38 resist reverse movement through the slot 36. To achieve this adjustable length fastening, the pairs of locking projections 38 have a transverse width at their widest points which exceeds the transverse width dimension of the slot 36. Preferably, the narrow neck portions 39 have a maximum transverse width dimension no greater than the transverse width dimension of the slot 36. This enables the strap 16 to lay flat against the nerve 18 when fastened. Further, the locking projections 38 are preferably shaped to assist in threading through the slot 36. For instance, with the arrow shape projections 38 of FIGS. 1-6, the double toothed lateral edges are tapered to narrow inwardly toward the leading edge 44 (free end) of the tail end portion 30. Each pair of projections 38 at its widest point has a transverse width that extends transversely beyond the slot width in an overlapping and locking mode. The extent of overlap of each projection 38 (i.e., on each side of the slot 36) compared to the transverse slot width is preferably at least about 10% of the slot width dimension, more preferably about 15-30%. This overlap of the projections resists reverse movement of the projections 38 through the slot 36. The length of the individual projections 38 and the number of longitudinally spaced paired projections 38 will vary to provide sufficient incremental adjustments around the nerve. The projection length and degree of overlap vary with such factors as the type and thickness of the elastomeric material, the nature (ex. size and weight) of the nerve interacting device 14, and the nature and size of the body tissue being encircled, so the above dimensions are provided only as guidelines. The taper of the arrow shaped projections 38 (narrowing toward the leading edge 44 of the tail end portion 30) provides a preferential sliding direction (in the insertion direction) when engaged in the slot 36. The tail end portion 30 may include a suture 40 and needle 42 at its leading edge 44 to assist in threading through the slot 36, and for locking and/or anchoring to the strap 16 once implanted (see FIGS. 9-11). The leading edge 44 might be formed with a suture connecting aperture 46, or the needle 42 can be used to attach to the leading edge 44 before or during implantation.

The strap 16 is wrapped circumferentially around the nerve 18 in order to create a good contact between the nerve 18 and the conductive elements 22, 24. Insulated leads 48, 50 and 52 are shown leading to a remote stimulator or recording device 54, which might be implanted or external to the patient. The conductive elements 22, 24 might be printed on, imbedded in or attached to (for example with adhesive) the inner face 32 of the body portion 26, by techniques known in the art. The conductive elements 22, 24 might be conductive metal or conductive rubber. Alternatively, the conductive elements might be designed to receive other than electrical impulses, for example one or more of thermal, auditory, vibrational, light or fluid stimulation.

Figure 3:
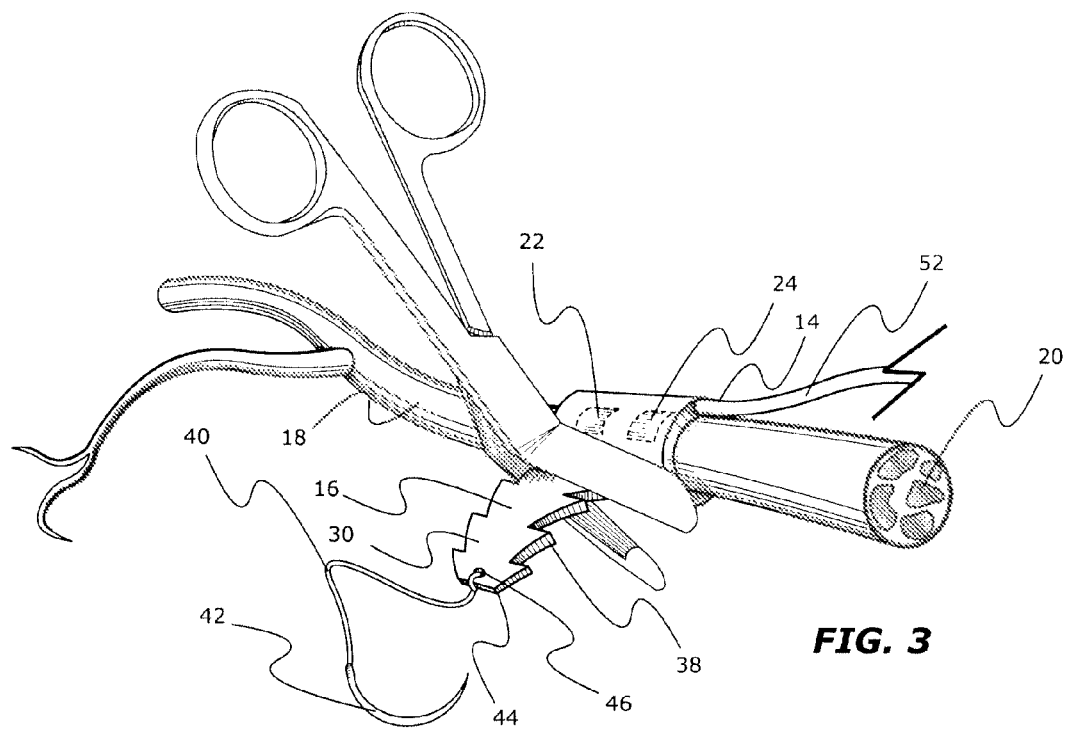
FIG. 3 is a schematic perspective view of the nerve cuff fitted around a nerve as in FIG. 1, illustrating the removal of the excess tail end with surgical scissors once the cuff is properly positioned.
Figure 4:
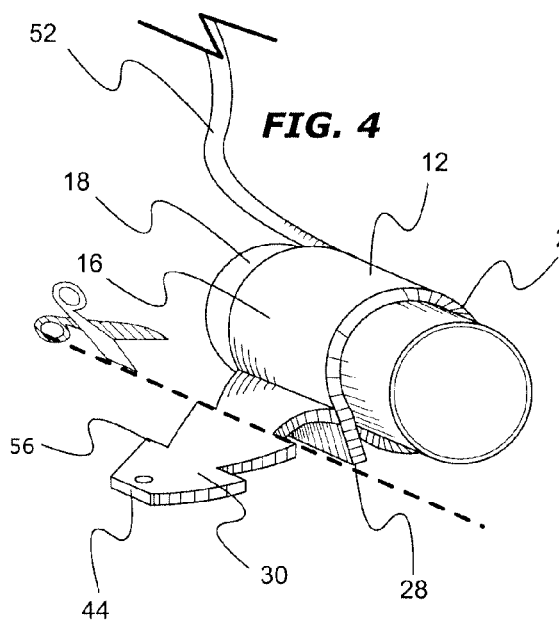
FIG. 4 is a schematic perspective view of a nerve cuff similar to that of FIG. 1 fitted around a large nerve.
Figure 5:
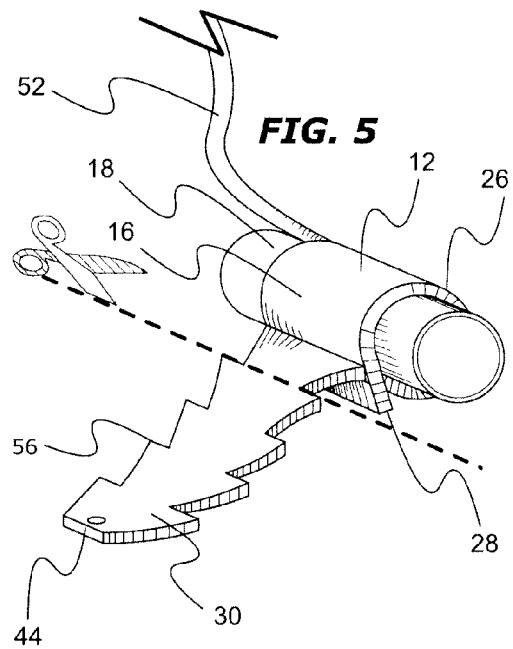
FIG. 5 is a schematic perspective view of a nerve cuff similar to that of FIG. 1 fitted around a small nerve.

As shown in FIGS. 3-5, once properly positioned the excess at the tail end portion 30 can be trimmed using medical scissors 55 to remove excess material and reduce mechanical irritation. The excess trimmed tail end material 56 (see FIGS. 4, 5) containing the suture 40 and needle 42 can then be discarded. FIGS. 4 and 5 show how the same sized nerve cuff 12 can wrap around two different sized nerves, a large nerve 18 in FIG. 4 and a smaller nerve 18 in FIG. 5. The small nerve 18 generates longer excess material 56 when compared to the excess material 56 from the large nerve 18, if cut the same distance (marked with a dotted line) from the projection 38 engaged in the head end slot 36.

Figure 6:
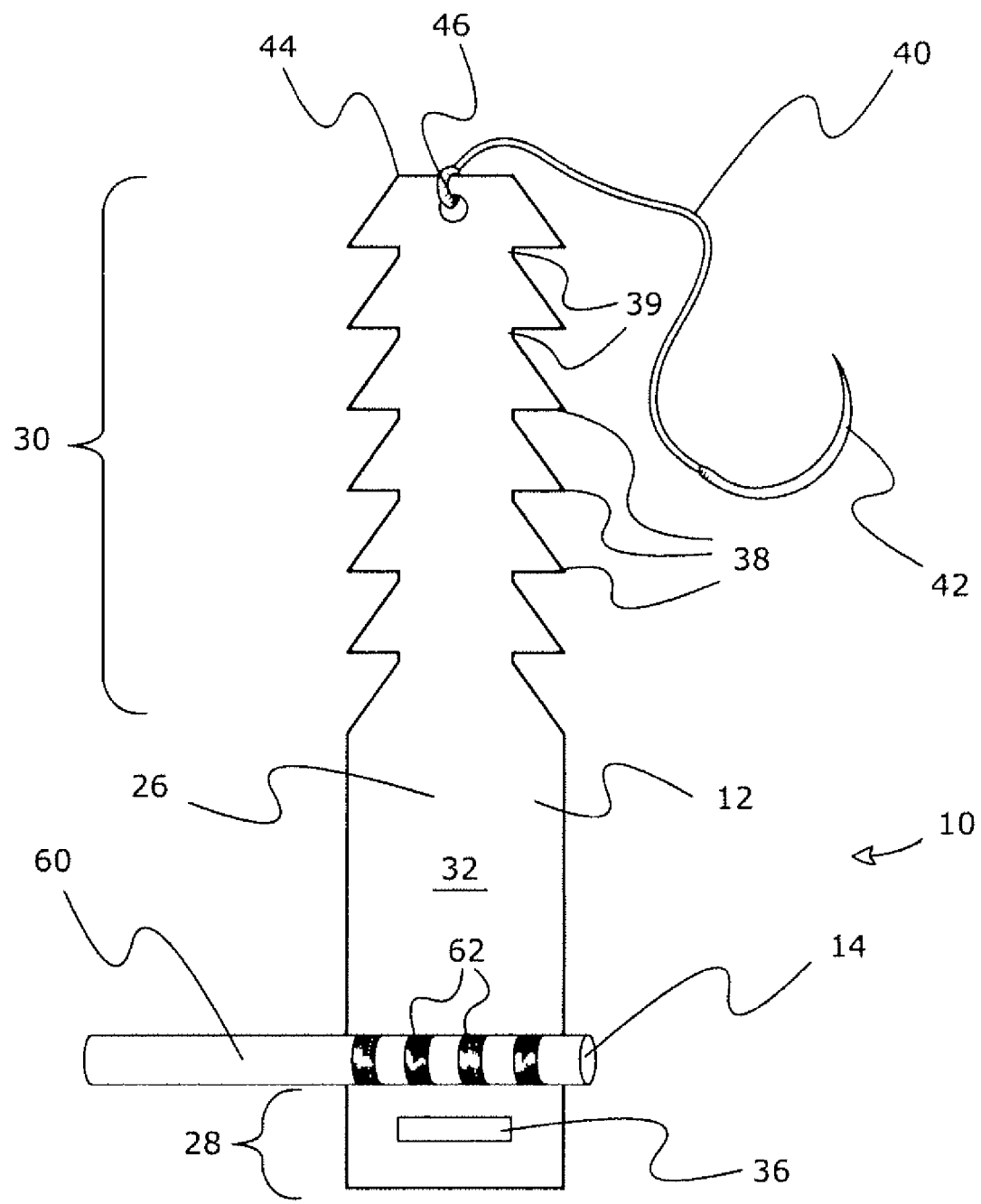
FIG. 6 is a schematic plan view of a nerve cuff similar to that of FIG. 1, but with a nerve interacting device in the form of a multiple contact electrode lead.
Figure 7:
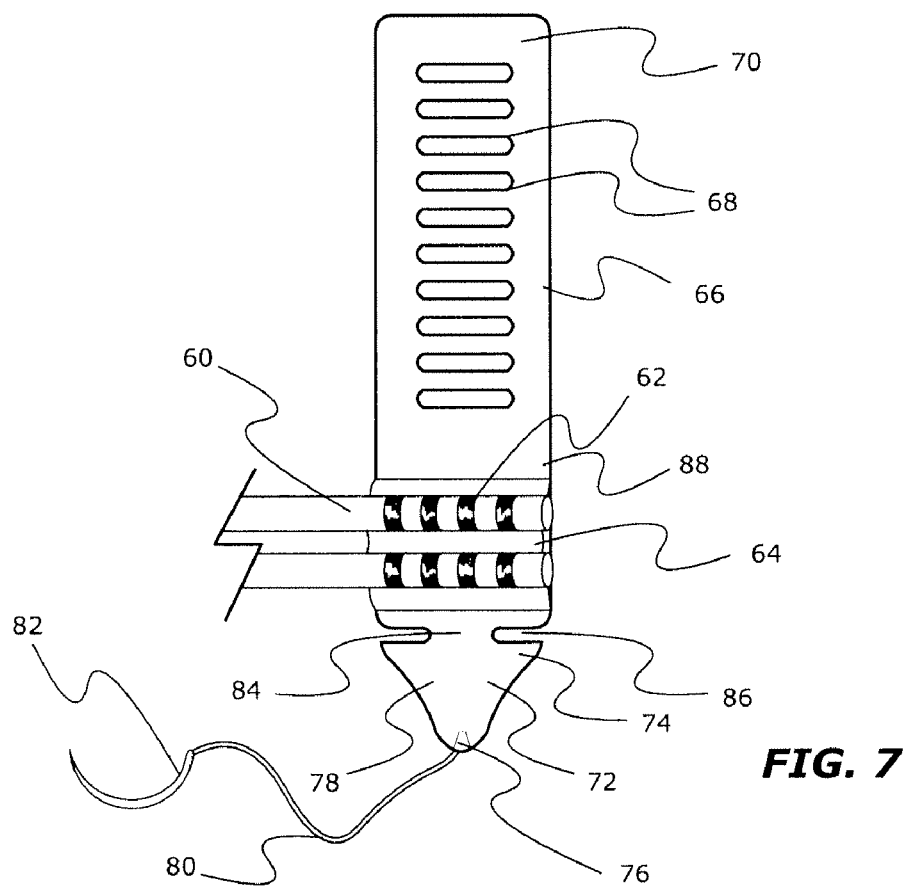
FIG. 7 is a schematic plan view of the inner face of a nerve cuff illustrating a belt embodiment of the adjustable closing cuff illustrating a belt embodiment of the adjustable closing mechanism with multiple locking apertures on the tail end of the cuff and showing two multiple contact electrode leads as nerve interacting devices.
Figure 8:
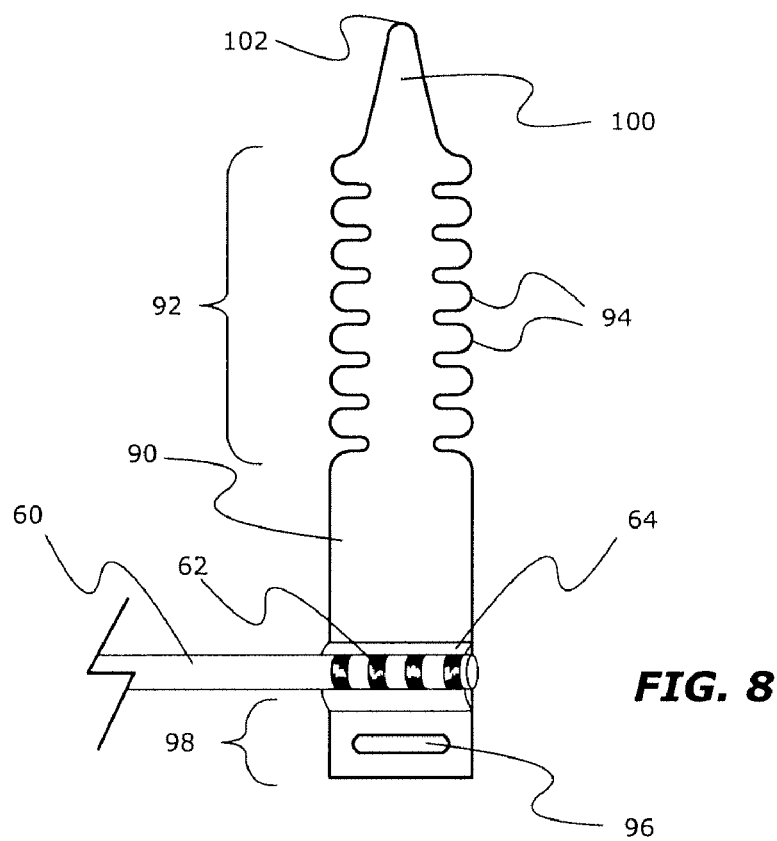
FIG. 8 is a schematic plan view of the inner face of a nerve cuff illustrating a further embodiment of a closing mechanism which resists movement equally in both directions once closed, and showing connection to a single multiple contact electrode lead as a nerve interacting device.

FIGS. 6-8 show alternate embodiments of a nerve cuff apparatus of this invention with nerve interacting devices in the form of one or more multiple contact electrode leads 60. Multiple contact electrode leads 60 include a plurality of conductive elements 62 in order to achieve a specific stimulation or recording result. These leads 60 might be simply held in place by simple wrapping with the nerve cuff 12, as in FIG. 6, or they might be held with a non-conductive biocompatible adhesive 64 as shown in FIGS. 7 and 8.

FIG. 7 illustrates an alternate closing/locking mechanism, namely a belt style closure. The strap 66 is formed with a plurality of longitudinally spaced slots 68 formed in the tail end portion 70. The head end portion 72 is formed with laterally paired locking projections 74. The leading edge 76 of the head end portion 72 forms an elongated lead tab 78 to assist in threading into one of the slots 68. The lead tab 78 may also be attached to a suture 80 and needle 82 as above described. The preferred width dimensions of the projections 74, narrower neck portion 84 and slots 68 are generally as set forth above. However, with the single pair of projections 74 of this embodiment, it is preferable that the space 86 adjacent the narrower neck portion 84 between the head and body portions 72, 88 has a length component no less than the thickness dimension of the strap 66. This assists in preventing the closure from re-opening.

In FIG. 8, the nerve cuff strap 90 is similar to that of FIG. 6, but the tail end portion 92 is formed with laterally paired projections 94 which are rounded, rather than tapered. These rounded projections 94 resist movement in both directions equally once fitted through the locking slot 96 formed in the head end portion 98. The strap 90 is formed with an elongated lead tab 100 at the leading edge 102 of the tail end portion 92 to facilitate threading the tail end portion 92 into the locking slot 96.

Figure 9:
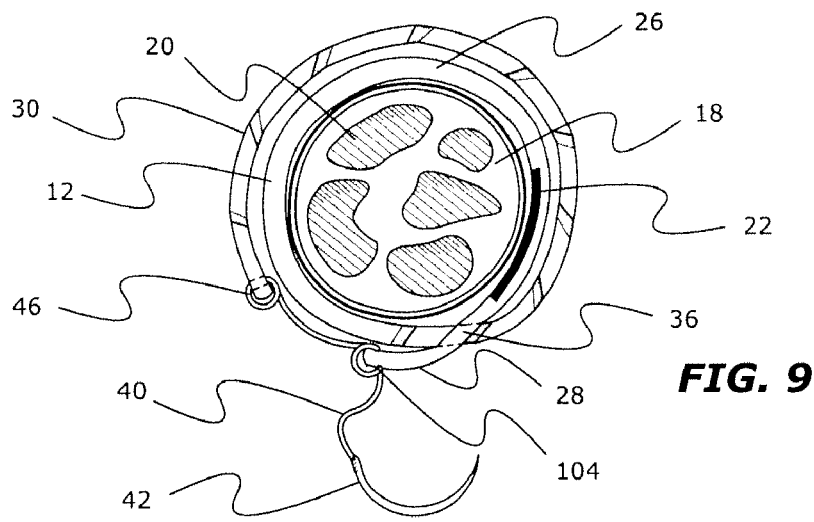
FIG. 9 is a side sectional and schematic view illustrating a method of locking the adjustable nerve cuff of FIG. 1 by wrapping it around the nerve and using a needle and suture to lock the cuff in place with a suture to the cuff itself.
Figure 10:
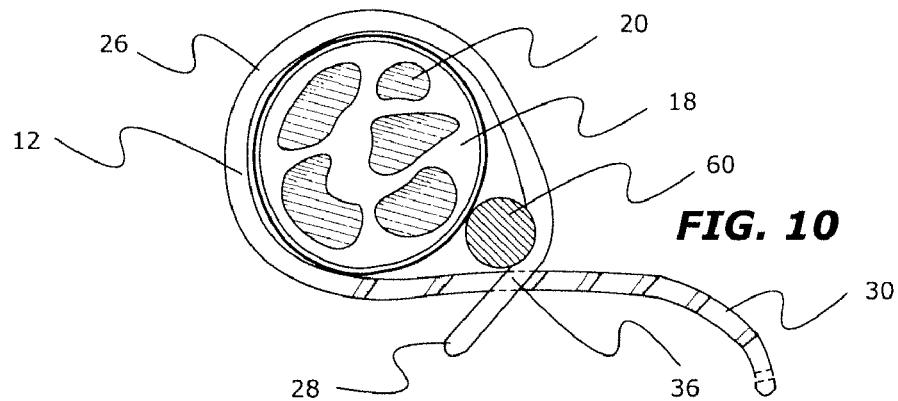
FIG. 10 is a side sectional and schematic view illustrating the nerve cuff of FIG. 6 prior to cutting and discarding the excess tail end.
Figure 11:
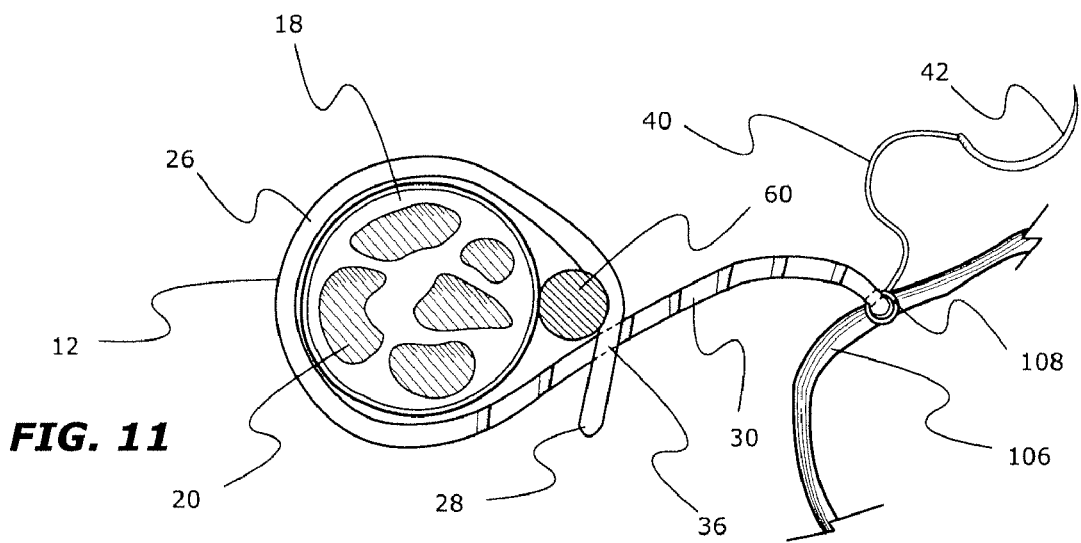
FIG. 11 is a side sectional and schematic view illustrating a method of anchoring the nerve cuff of FIG. 6 to nearby body tissue.

FIGS. 9-11 illustrate cross sectional views of different possible anchoring and locking methods for a nerve cuff 12 similar to that of FIGS. 1 or 6. To lock the nerve cuff 12 in place it is possible to wrap the excess at the tail end portion 30 around the cuff 12, as seen in FIG. 9. To prevent the cuff 12 from unraveling, the needle 42 and suture 40 can be used to tie the head end portion 28 with the tail end portion 30 via a stitch 104. This reduces the chance of the nerve cuff 12 unraveling, and can be used to optimize contact between the conductive elements 22, 24 and the nerve 18. The cuff 12 can also be left as is once the tail end portion 30 has been inserted into the head end portion 28 as shown in FIG. 10 (or this tail end portion 30 may be cut as described above). The suture 40 and needle 42 can also be used to anchor the entire cuff 12 to nearby tissue 106 by stitching the tail end portion 30 via a stitch 108 to the nearby tissue 106, as seen in FIG. 11.

Figure 12:
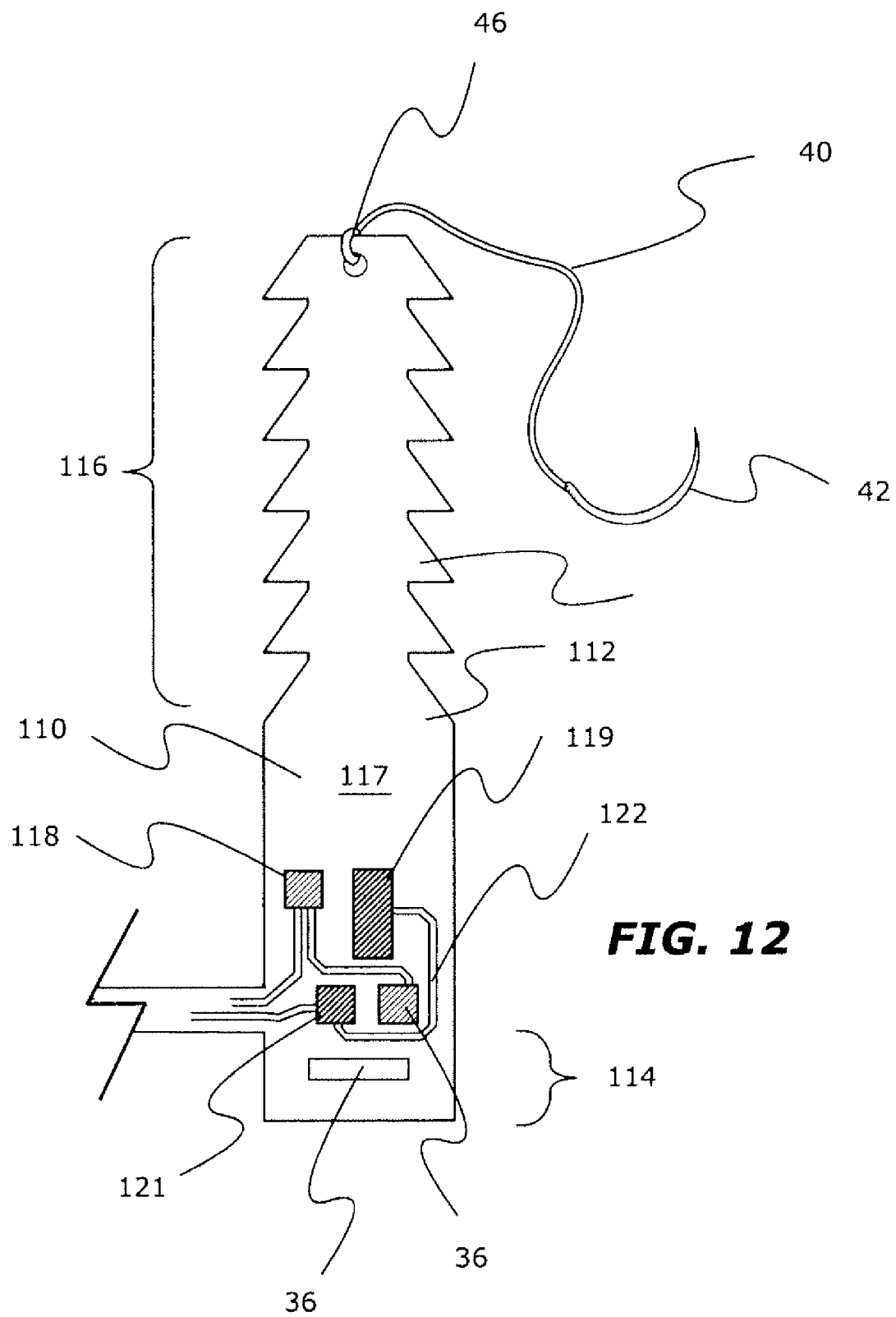
FIG. 12 is a schematic plan view of the inner face a nerve cuff with a closing mechanism similar to that of FIGS. 1 and 6, but formed with custom printed connections as the nerve interacting device.

In FIG. 12 the nerve interacting device (or other tissue interacting device) may take the form of a circuit printed the body portion 110 of a nerve cuff strap 112, between the head end and tail end portions 114, 116. In FIG. 12, the inner face 117 of the body portion 110 is shown, but the circuit components might be printed on either or both sides, or the components may be imbedded in the strap 112. The closing mechanism is similar to that shown in FIG. 6. The processes of photolithography and electroplating can be used to generate custom conductive element contact points 118, 119, 120, 121 that are unique in size and location to suit the nerve or tissue interacting device application. Some of these contact points 118-121 can be linked to each other with conductive but insulated tracks 122.

Figure 13:
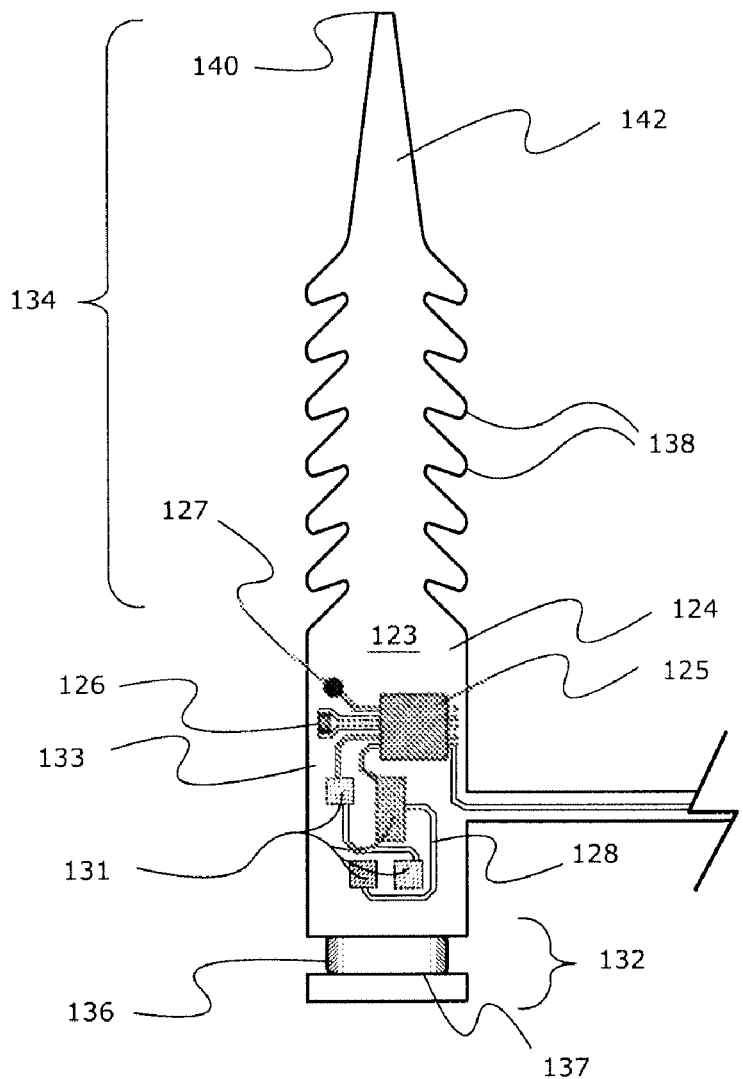
FIG. 13 is a schematic plan view of the outer face of a nerve cuff with printed connections and imbedded electronics and having a loop closing mechanism.
Figure 14:
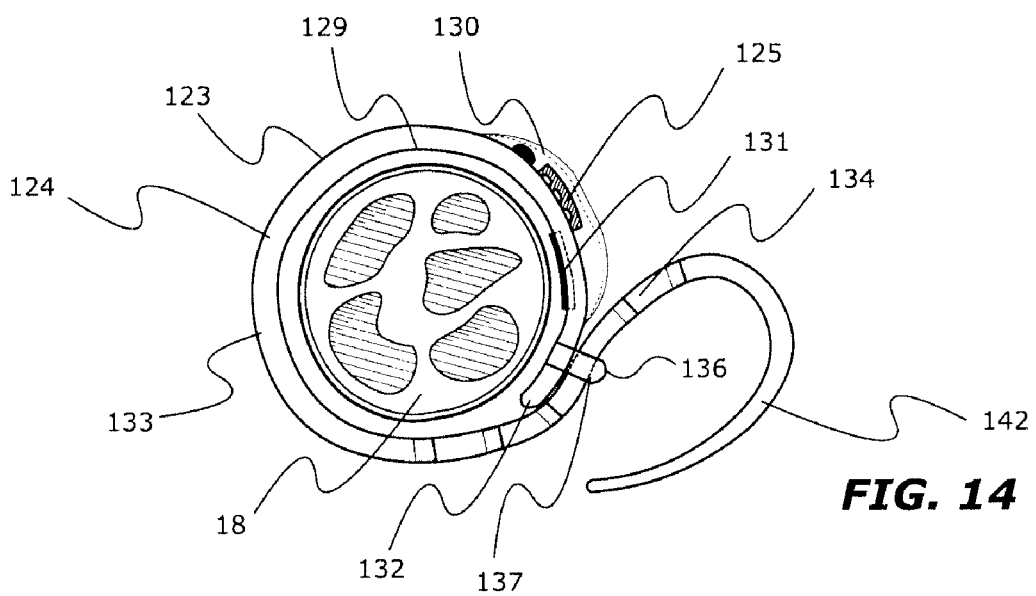
FIG. 14 is a side sectional and schematic view of the installed nerve cuff of FIG. 13 with printed connections and fully imbedded electronics, showing the loop closing mechanism in its locked position around the nerve.

In FIGS. 13, 14, an electronic circuit is shown on the outer face 123 of a nerve cuff strap 124. Printing techniques as above-mentioned can be used to create electric circuits such as pre-amplifiers, or entire stimulator/recording devices that can be placed directly on the of the strap 124. Exemplary electronic components are shown as a micro processor 125, resistor 126, and capacitor 127, connected with can be connected with conductive and insulated tracks 128. These are shown on the outer face 123 in FIGS. 13, 14, with the electrical contacts 131 being shown on the inner face 129 for contact with the nerve 18. The entire electronic assembly on the outer face 123 can be covered in an insulating biocompatible material 130 such as silicone rubber to prevent direct tissue interaction with the electronics.

FIGS. 13, 14 also illustrate another embodiment for length adjustable closing mechanism. The strap 124 with head and tail end portions 132, 134, and body portion 133, has a loop 136 (ex. ring) formed at the head end portion 132. The loop 136 sits above the plane of the strap 124, and may be connected to the strap 124, for example by a biocompatible adhesive. The opening 137 formed between the strap 124 and the loop 136 functions as a locking aperture to secure the laterally paired locking projections 138 formed on the tail end portion 134. As above, the width of the pairs of projections 138 at their widest points is greater than the transverse width of the loop opening 137. When the tail end portion 134 is threaded through the loop 136, the loop 136 rests on top of the head end portion 132 (best seen in FIG. 14). The loop 136 might be provided as a separate ring which is attached by adhesive, similar to the figures. Alternatively, the loop 136 and strap 124 can be made from a single thin insulating, flexible sheet of biocompatible material by folding side wings (not shown) inwardly to form the loop 136, and fixing with adhesive. The shape of the pairs of projections 138 shown in FIG. 13 is generally tear drop shaped with extra downward taper (toward the body portion 133), for ease of insertion in the loop 136, and to increase the resistance to reverse movement through the loop 136 once fastened in the loop 136. These tear drop shaped projections 138 may also be used in slot embodiments (see FIG. 19). The leading edge 140 of the tail end portion 134 is formed with an elongated lead tab 142 having a transverse width at its leading edge 140 which is substantially smaller than the transverse width of the loop opening 137. This facilitates insertion of the tail end portion 134 through the opening 137.

Figure 15:
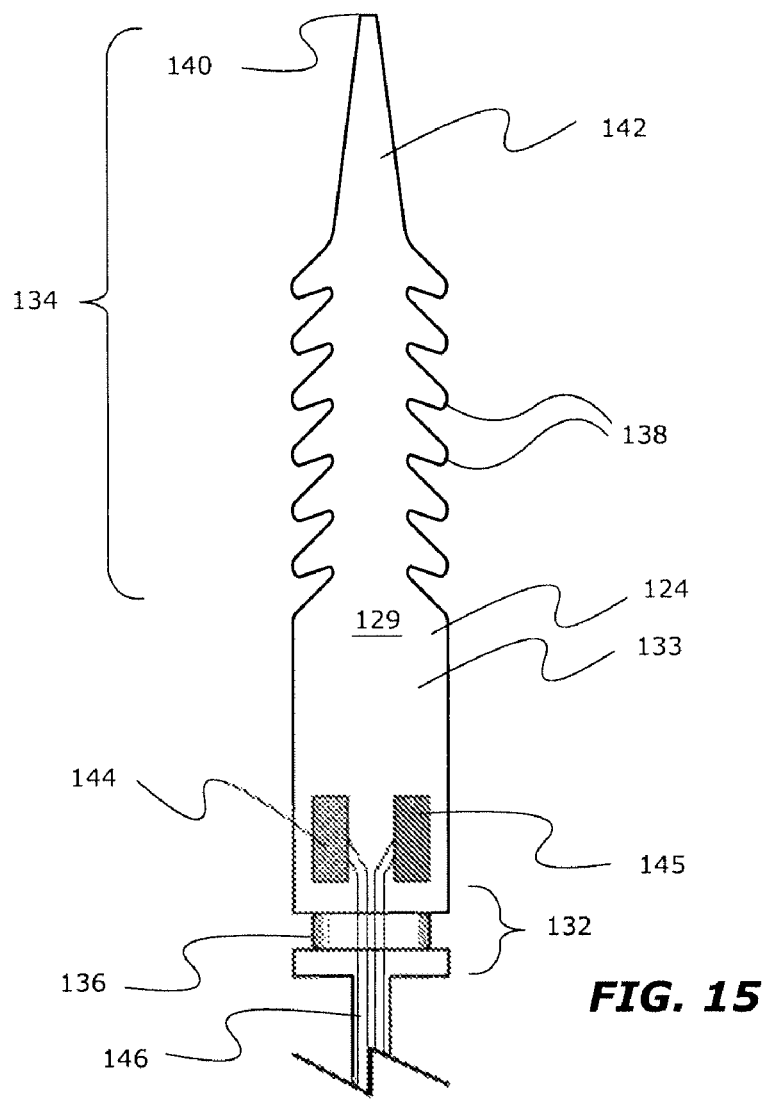
FIG. 15 is a schematic plan view of the inner face of a nerve cuff with the closing mechanism similar to that of FIG. 13, but showing a perpendicular electrode lead, and having printed conductive elements on the inner face of the nerve cuff.
Figure 16:
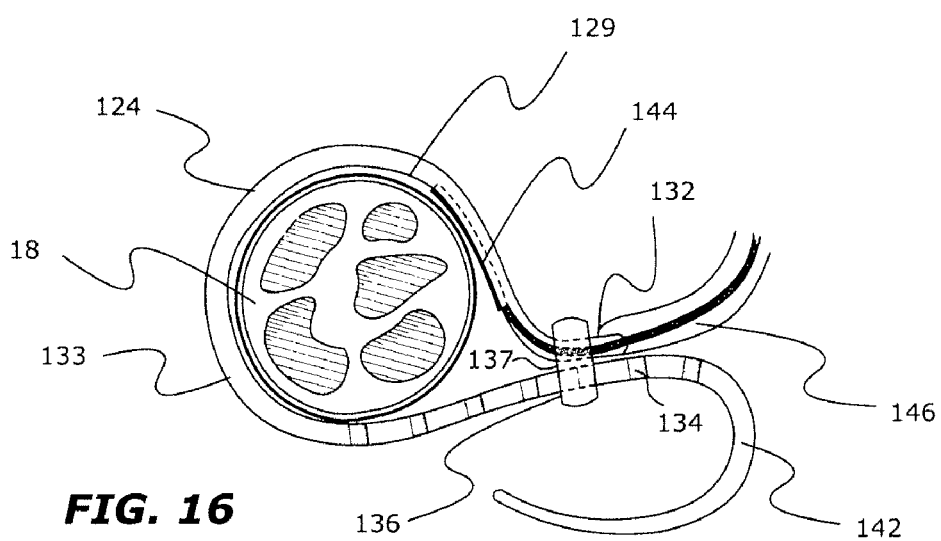
FIG. 16 is a side sectional and schematic view of the nerve cuff of FIG. 15 in its locked position around the nerve.

In some applications it may be important to orient an electrode lead facing perpendicularly to a nerve. A nerve cuff apparatus to accommodate this orientation is shown in FIGS. 15, 16. This orientation may be advantageous in endoscopic procedures. The nerve cuff strap 124 is similar to that of FIGS. 13, 14, so FIGS. 15, 16 show like components with the same reference numerals. However, FIG. 15 shows the inner face 129 printed with conductive elements 144, 145 for electrical contact with the nerve 18. The insulated leads 146 from the elements 144, 145 are oriented to be perpendicular to the nerve 18 on implantation (rather than parallel as in previous embodiments). This is the ideal application for the loop closure mechanism. In FIG. 16, the loop 136 is shown in the closed position to orient the opening 137 above the inner face 129 (the strap is shown with the outer face 123 in FIG. 14, so the loop opening 137 there is above the outer face 123).

Figure 17:
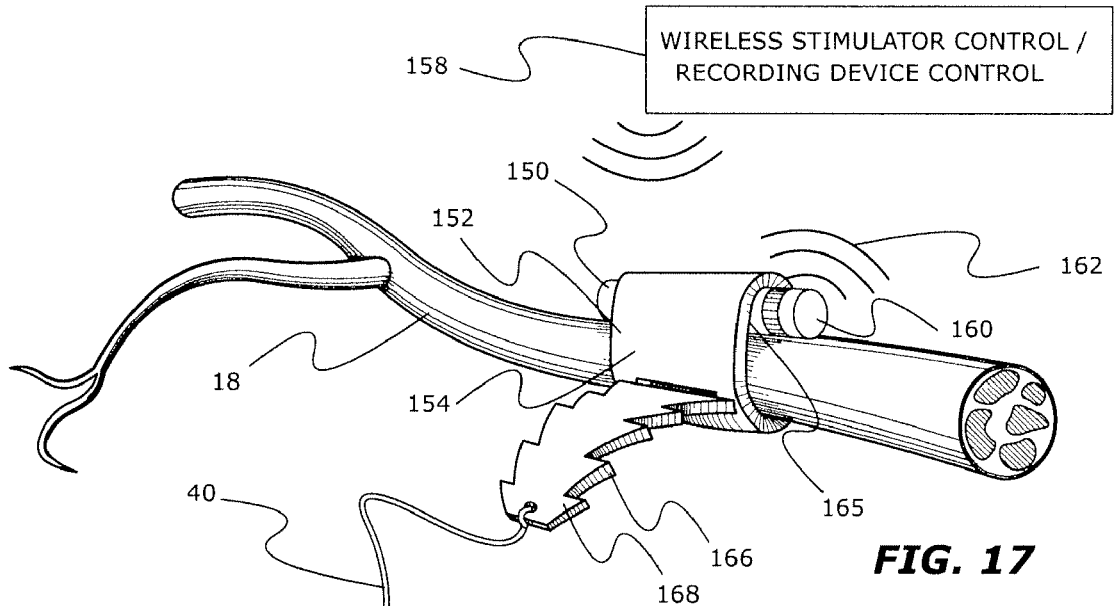
FIG. 17 is a schematic perspective view of a nerve cuff fitted around a nerve and holding a BION™ wireless stimulator device in proximity to the nerve. The BION has an antenna for wireless transmission to a stimulator control or recording device control unit.
Figure 18:
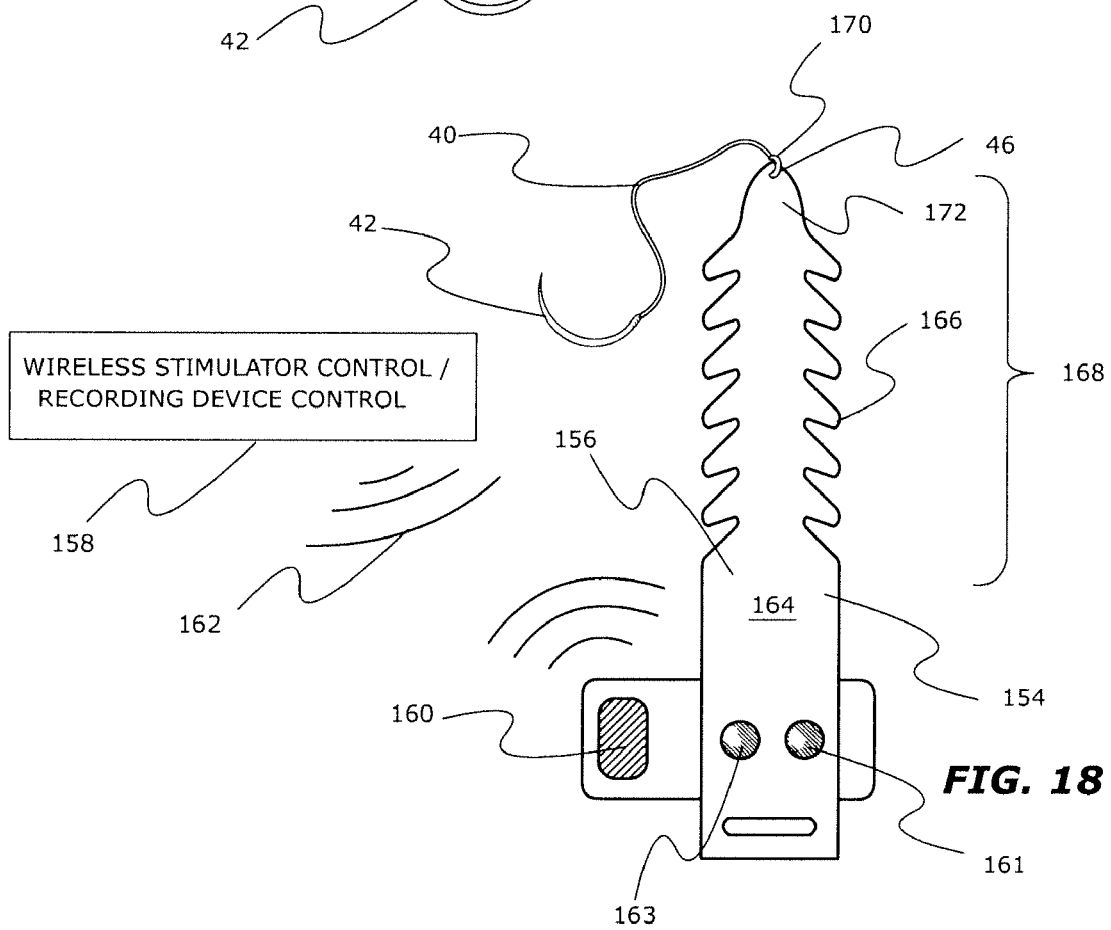
FIG. 18 is a schematic plan view of the inner face of a nerve cuff showing conductive elements on the inner face of the nerve cuff and a wireless antenna device on the outer face of the nerve cuff for wireless transmission to a stimulator or recording device control unit.

FIGS. 17 and 18 illustrate a complete wireless stimulator anchored in immediate proximity to the nerve 18. In FIG. 17, a wireless stimulator 150 such as a BION™ from Advanced Bionics, LLC of California (see for example U.S. Pat. No. 5,193,539 to Schulman et al.) is attached with adhesive (not shown) to the inner face 165 of the body portion 154 of the nerve cuff strap. The BION 150 is a self sufficient unit with an outer shell that is conductive for electrical contact with the nerve 18. The BION receives data and/or power from an external control or recording unit 158 via an antenna 160 on the BION unit 150. Radio waves 162 (or other frequency waves) may be used to control the unit 150 or transmit to the controller/recorder 158. The nerve apparatus of the embodiment in FIG. 18 has conductive elements (example metal contacts) 161, 163 printed, attached or imbedded at the inner face 164 of the body portion 154 of strap 156 for direct contact with the nerve 18 once installed. The wireless control or recording unit 158 can be located externally to the patient, or may be implanted. The laterally paired projections 166 on the tail end portion 168 are shown as arrow shaped in FIG. 17 (as in FIG. 6) with needle 42, suture 40, and tear drop shaped in FIG. 18 (similar to FIG. 13). The leading edge 170 in FIG. 18 is shown as forming an elongated tab 172, connected to needle 42 and suture 40, similar to that in earlier figures.

It will be evident that alternate interlocking shapes of laterally paired projections and/or locking apertures may be used in this invention. For example, the slots might be more oval shaped or circular shaped, with the projections being similarly altered so as to still project in a transverse width direction beyond the transverse width dimension at the widest point of the slot. Alternatively, the projections might be shaped in 3D (and not just in 2D) to lock in the locking aperture to resist movement in the reversing direction. However, the above-described 2D embodiments are preferred for their manufacturing simplicity and low cost, as well as for their ease of manipulation during implantation.

The tissue interacting devices useful in the tissue cuff apparatus of this invention are wide ranging, with the above and following descriptions serving only as exemplary embodiments. Nerve stimulating devices are well known in the prior art. Nerve recording devices are also known. For example, nerve recordings from sacral root recordings intra-operatively as electroneurographic (ENGs) signals may be obtained from either free electrodes or nerve cuffs. These are common in procedures for spinal cord injured patients that focus on the sacral roots of the spinal cord. Devices that have both stimulation and recording capabilities might also be used, such as shown in U.S. Pat. No. 5,913,882 to King, designed for augmenting electrical stimulation usefulness in pain control. Similarly, devices for sleep apnea via vagal nerve stimulation, or devices for Parkinson's disease in the form of deep brain stimulation, might be used with the nerve cuff of this invention.

The substrate materials for the strap extend to elastomeric materials which provide sufficient elasticity, resiliency and strength in a thin flat format, without the corrugations, undulations or piercing projections of the prior art. The materials are biocompatible for implantation, and are preferably non-conductive to protect/insulate surrounding body tissue from any conductive elements (typically electrical contacts). Exemplary materials include flat sheets of silicone rubber elastomers, for example PDMS (polydimethylsiloxane), Silastic™ (a silicone rubber), and biocompatible polyurethane polymers, and biocompatible polyimides. Generally, the sheets have a uniform thickness so that the strap is formed with a uniform thickness. However, the strap might alternatively be formed with increased thickness in the certain body, head or tail portions to increase the strength of one or more of these sections for particular applications. Other elastomeric biocompatible materials will be known to those skilled in the biomedical area. The substrate material may be coated or impregnated with one or more active tissue agents, such as antibiotics, proteins, growth factors and the like, for applications such as healing.

For applications involving adhesives, the adhesives are biocompatible, with exemplary materials including silicone rubber, cyanoacrylates, and polyethylene glycol polymers. The latter group are advantageous in applications where a biodegradable adhesive is desired.

Manufacturing involves the shaping, cutting or stamping of a sheet of non-conductive biocompatible elastomeric material. Laser cutting is preferred, particularly for the fine details and dimensions of the projections and slots. The conductive elements (for example conductive metals or conductive rubber) may be imbedded, attached or printed into or on the sheet. The entire cuff apparatus can then be sterilized prior to implantation.

Advantages and other features of the invention include:
1. One size fits various nerve sizes or configurations. The exact nerve sizes are typically not known in advance of implantation, so the length adjustability for intra-operative manipulation provides a more secure and stable attachment to the nerve, limiting additional surgical procedures needed in the event of device migration.
2. Once fastened, the excess material in the tail end portion of the nerve cuff can be trimmed or sutured shut. The excess tail end material might alternatively serve as anchoring material by suturing to surrounding body tissue.
3. The adjustable fastening mechanism allows for intra-operative adjustment for different nerve sizes and re-positioning around the nerve until the desired result is obtained, minimizing post operative failures or migration of the apparatus.
4. The initial flat configuration makes the cuff easy to sterilize, manufacture and insert around the nerve.
5. The body portion being clear of the fastening head and tail end portions, allows for use with a wide range of conductive elements and nerve interacting devices. For instance, metal conductive elements and circuits can be printed on the inner face of the flat body portion in unique arrangements. In addition, or alternatively, other circuit components may be imbedded into the body portion or otherwise attached (similar to electronic boards). The outer face of body portion may also carry circuit components, or serve to attach nerve interacting devices. Alternatively, Silastic materials can accommodate conductive and non-conductive rubber instead of printed metal. Alternatively, the body portion can accommodate multiple conductive contacts, and can be used to secure a traditional barb/tube electrode close to the nerve. Still alternatively, a BION may be secured close to the nerve with the nerve cuff to prevent shifting.
6. The needle and suture at the tail end allows for intuitive and minimally destructive approach to installing the cuff (as a guide). The needle may be metal, and the suture a traditional suture. Alternatively, the needle might be plastic, and the suture a thin sheet of rubber.

EXAMPLE

The nerve cuff apparatus of this invention in multiple of the preferred embodiments has been tested in numerous animal trials where the application was an electrical nerve cuff. Following successful animal implanting, a plurality of nerve cuff apparatus 180 having the configuration and dimensions shown in FIG. 19 (not drawn to scale) were implanted in a 51 year old spinal cord injured man. The implantation was directed to restore upper extremity hand function in conjunction with a nerve stimulator device as described in U.S. Patent Application No. 2006/0184211 A, published Aug. 17, 2006, to Gaunt et al. The nerve cuff straps 182 were each laser cut out of a biocompatible silicone rubber sheet 0.254 mm thick. The implanted nerve cuff apparatus 180 included a monopolar conductor 184 attached to the body portion 186 of the nerve cuff strap 182 with a silicone rubber adhesive 188, cured prior to sterilization and implantation. The tail end portion 190 was formed with tear drop shaped projections 194 as shown, and an elongated lead tab 196 to aid in manipulating into the slot 198 formed in the head end portion 200. The head end portion 200 of the nerve cuff strap 182 was lengthened with excess length material in order to aid in manipulation of the cuff apparatus 180 during implantation. The nerve cuff apparatus 180 once circumferentially attached to the target nerves was tested with stimulation to verify proper positioning. Position was adjusted on each of the three implanted cuffs during the implantation procedure (i.e., intra-operatively), until the most favorable results were observed. Each cuff apparatus 180 was then trimmed (both the head and tail end portions 200, 190) with surgical scissors (as shown in FIG. 3). Five months later, all three implantation sites continued to stimulate the desired nerves, with no sign of apparatus migration or failure.

As used herein and in the claims, the word "comprising" is used in its non-limiting sense to mean that items following the word in the sentence are included and that items not specifically mentioned are not excluded. The use of the indefinite article "a" in the claims before an element means that one of the elements is specified, but does not specifically exclude others of the elements being present, unless the context clearly requires that there be one and only one of the elements. For example, the term "a slot" as used herein and in the claims may include multiple slots.

All references mentioned in this specification are indicative of the level of skill in the art of this invention. All references are herein incorporated by reference in their entirety to the same extent as if each reference was specifically and individually indicated to be incorporated by reference. However, if any inconsistency arises between a cited reference and the present disclosure, the present disclosure takes precedence. Some references provided herein are incorporated by reference herein to provide details concerning the state of the art prior to the filing of this application, other references may be cited to provide additional or alternative device elements, additional or alternative materials, additional or alternative methods of analysis or application of the invention.

The terms and expressions used are, unless otherwise defined herein, used as terms of description and not limitation. There is no intention, in using such terms and expressions, of excluding equivalents of the features illustrated and described, it being recognized that the scope of the invention is defined and limited only by the claims which follow. Although the description herein contains many specifics, these should not be construed as limiting the scope of the invention, but as merely providing illustrations of some of the embodiments of the invention.

One of ordinary skill in the art will appreciate that elements and materials other than those specifically exemplified can be employed in the practice of the invention without resort to undue experimentation. All art-known functional equivalents, of any such elements and materials are intended to be included in this invention within the scope of the claims, including without limitation the options and alternatives mentioned herein. The invention illustratively described herein suitably may be practiced in the absence of any element or elements, limitation or limitations which is not specifically disclosed herein.

The invention claimed is:

1. An implantable, circumferentially adjustable tissue cuff to enable circumferential attachment to an internal body tissue, the cuff comprising:
   a flat, thin, elastomeric strap formed of a biocompatible non-conductive material, the strap being elongated along a longitudinal axis, the strap having a body portion connected between a tail end portion and a head end portion, and a length in excess of a circumference of the internal body tissue, wherein the length in excess of the circumference of the internal body tissue is provided in one or both of the head end portion and the tail end portion;
   the tail end portion and the head end portion being configured for adjustable length fastening one to the other when wrapped around the internal body tissue with a configuration of either:
   a) the tail end portion being formed with a plurality of longitudinally spaced, laterally paired locking projections and the head end portion being formed with one or more locking apertures; or
   b) the tail end portion being formed with a plurality of longitudinally spaced locking apertures and the head end portion being formed with one or more laterally paired locking projections; and
   each of the laterally paired locking projections being shaped to allow for passage through the locking apertures by flexing of the locking projections in an insertion direction through the locking aperture, and to restrict movement in a reversing direction through the locking aperture.

2. A tissue cuff apparatus to enable circumferential attachment of a tissue interacting device to an internal body tissue, said tissue cuff apparatus comprising a tissue cuff as defined in claim 1 and one or more implantable tissue interacting devices attached to, imbedded in, or printed on the body portion of the strap, wherein the tissue interacting device includes one or more conductive elements adapted to be in conducting proximity to the internal body tissue when the strap is wrapped around the body tissue.

3. The tissue cuff apparatus of claim 2, wherein the tissue interacting device is adapted to stimulate or record the body tissue, and wherein the one or more conductive elements is adapted to respond to one or more of electrical, thermal, auditory, vibrational, light or fluid stimulation.

4. The tissue cuff apparatus of claim 3, wherein the one or more conductive elements comprise one or more electrical contacts on an inner face of the body portion of the strap.

5. The tissue cuff apparatus of claim 4, further comprising insulated leads connecting the one or more electrical contacts to a remote stimulating or recording device.

6. The tissue cuff apparatus of claim 3, wherein the tissue interacting device is an electrode lead or a conductor adapted to be held in contact with the body tissue by the strap.

7. The tissue cuff apparatus of claim 3, wherein the tissue interacting device is a wireless stimulator adapted to be attached to the strap or to be held in contact with the body tissue.

8. A method for circumferentially attaching a tissue cuff to an internal body tissue, the method comprising the steps of:
   i. providing the tissue cuff as defined in claim 1;
   ii. implanting the tissue cuff by wrapping the strap circumferentially around the internal body tissue; and iii. fastening the tail end portion and the head end portion together with an appropriate one of the laterally paired locking projections and locking apertures, whereby the plurality of locking apertures or the plurality of laterally paired projections allow for a circumference of the tissue cuff to be adjusted intra-operatively to a particular circumference of the internal body tissue.

9. The method of claim 8, wherein an excess of the strap remaining in the tail end portion or the head end portion after fastening is removed by cutting.

10. The method of claim 8, wherein an excess of the strap remaining in the tail end portion or the head end portion after fastening is sutured to the strap or to surrounding tissue to anchor the tissue cuff.

11. The method of claim 8, wherein an excess of the strap remaining in the tail end portion or the head end portion after fastening is fastened to the strap with a biocompatible adhesive.

12. The method of claim 8, further comprising providing one or more implantable tissue interacting devices attached to, imbedded in or printed on the body portion of the strap, the tissue interacting device including one or more conductive elements adapted to held in conducting proximity to the body tissue when the strap is wrapped around the body tissue, and wherein the internal body tissue is a nerve.

13. The tissue cuff of claim 1, wherein the body portion is integral with the head end portion and the tail end portion, and wherein the body portion has a length which is not greater than the circumference of the internal body tissue.

14. The tissue cuff of claim 13, wherein:
the tail end portion and the head end portion are configured as in (a);
the one or more locking apertures is a slot having a transverse width dimension; and
each pair of locking projections has a transverse width dimension at a widest point which is greater than the transverse width dimension of the slot.

15. The tissue cuff of claim 14, wherein the plurality of laterally paired locking projections are longitudinally spaced by narrower neck portions, and the neck portions have a transverse width dimension which is no greater than the transverse width dimension of the slot.

16. The tissue cuff of claim 15, wherein each pair of the locking projections is generally arrow shaped to resist movement in the reversing direction.

17. The tissue cuff of claim 15, wherein each pair of the locking projections is generally tear drop shaped to resist movement in the reversing direction.

18. The tissue cuff of claim 15, wherein each pair of locking projections is rounded to resist movement through the slot in both the insertion and reversing directions.

19. The tissue cuff of claim 15, further comprising a suture connected to the tail end portion of the strap, and a needle connected to the suture.

20. The tissue cuff of claim 15, wherein the tail end portion is formed with an elongated lead tab at its free end, the lead tab having a transverse width at a lead end which is less than the transverse width of the slot to facilitate insertion of the tail end portion through the slot.

21. The tissue cuff of claim 15, wherein the head end portion is formed with a loop that forms the locking aperture.

* * * * *